United States Patent [19]

Guindon et al.

[11] Patent Number: 5,021,447

[45] Date of Patent: Jun. 4, 1991

[54] TETRAHYDROCARBAZOLE 1-ALKANOIC ACIDS AND PHARMAECUTICAL COMPOSITIONS

[75] Inventors: Yvan Guindon; Christiane Yoakim, both of Montreal; John W. Gillard, Baie d'Urfe; Yves Girard, Ile Bizard, all of Canada

[73] Assignee: Merck Frosst Canada, Inc., Kirkland, Canada

[21] Appl. No.: 268,824

[22] Filed: Nov. 7, 1988

Related U.S. Application Data

[60] Division of Ser. No. 76,424, Jul. 21, 1987, Pat. No. 4,808,608, which is a continuation-in-part of Ser. No. 1,739, Jan. 9, 1987, abandoned, which is a continuation-in-part of Ser. No. 821,726, Jan. 23, 1986, abandoned.

[51] Int. Cl.$^5$ .................... A61K 31/40; C07D 209/82; C07D 209/86
[52] U.S. Cl. ..................................... 514/411; 548/439
[58] Field of Search .......................... 548/439; 514/411

[56] References Cited

U.S. PATENT DOCUMENTS 3,896,145  7/1975  Berger et al. ...................... 548/444
4,009,181  2/1977  Berger et al. ...................... 548/439
4,057,559  11/1977  Asselia et al. ...................... 548/439

*Primary Examiner*—Robert W. Ramsuer
*Attorney, Agent, or Firm*—Lopez, Gabriel; DePrima, Joseph F.

[57] ABSTRACT

Tetrahydrocarbazole 1-alkanoic acids are disclosed. The compounds act as prostaglandin and thromboxane antagonists and are useful in treating asthma, diarrhea, hypertension, angina, platelet aggregation, cerebral spasm, premature labor, spontaneous abortion and dysmenorrhea and as cytoprotective agents.

9 Claims, No Drawings

TETRAHYDROCARBAZOLE 1-ALKANOIC ACIDS AND PHARMAECUTICAL COMPOSITIONS

RELATED CASES

This is a division of Ser. No. 076,424, Jul. 21, 1987, U.S. Pat. No. 4,808,608, which is a continuation-in-part of Ser. No. 001,739, Jan. 9, 1987, abandoned, which is a continuation-in-part of Ser. No. 821,726, Jan. 23, 1986, abandoned.

BACKGROUND OF THE INVENTION

This invention relates to prostaglandin antagonists useful in treating a variety of conditions, such as allergic asthma where excessive contractile activity of prostaglandins and prostaglandin biosynthetic intermediates occur.

These compounds antagonize the actions of contractile prostaglandins, such as $PGF_{2\alpha}$, $PGG_2$, $PGH_2$, $PGD_2$ and $TXA_2$. The use of agents which act as prostaglandin antagonists offers new approaches to therapy in a number of disease states. For example, certain prostaglandins, such as $PGF_{2\alpha}$, $PGD_2$, $PGG_2$, and $PGH_2$, are potent bronchospastic agents. Indeed human asthmatics have been shown to be especially sensitive to the bronchial constricting action of $PGF_{2\alpha}$.

DESCRIPTION OF THE INVENTION

The present invention relates to novel comPounds of Formula I:

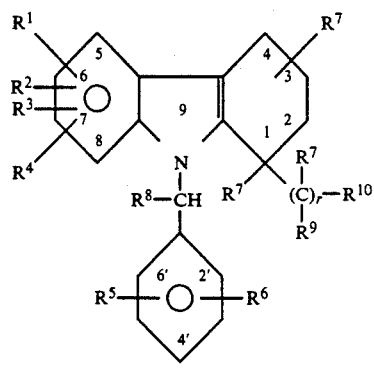

wherein:
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) —$(CH_2)_n$M
wherein n is 0 to 3 and M is
a) $OR^{13}$;
b) halogen;
c) $CF_3$;
d) $SR^{13}$;
e) phenyl or substituted phenyl wherein substituted phenyl is as defined below in the definition of
f) $COOR^{14}$;
g)

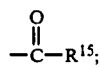

h) tetrazole;

i)

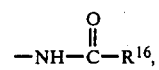

wherein $R^{16}$ is $C_1$ to $C_6$ alkyl, benzyl or phenyl;
j) —$NR^{14}R^{14}$;
k) —$NHSO_2R^{17}$ wherein $R^{17}$ is $C_1$ to $C_6$ alkyl, 4-methylphenyl, phenyl, or $CF_3$;
l)

$$-\overset{\overset{O}{\|}}{C}-CH_2OH;$$

m) —$SOR^{13}$;
n) —$CONR^{14}R^{14}$;
o) —$SO_2NR^{14}R^{14}$;
p) —$SO_2R^{13}$;
q) $NO_2$;
r)

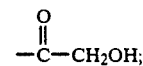

s)

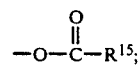

t)

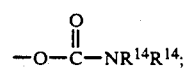

v) $N_3$;
u) $CN$;
$R^7$ is H or alkyl of 1 to 6 carbons;
$R^8$ is H or alkyl of 1 to 6 carbon atoms;
each $R^9$ is independently H, OH, $C_1$ to $C_4$-0-alkyl or alkyl of 1 to 4 carbons;
$R^{10}$ is COOH; $CH_2OH$; CHO; tetrazole; $NHSO_2R^{11}$ wherein $R^{11}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or to 1 to 6 carbons; $CONHSO_2R^{11}$; hydroxymethylketone; CN; or $CON(R^9)$;
r is 1 to 6;
each $R^{13}$ independently is H; $C_1$ to $C_6$ alkyl; benzyl; phenyl or substituted phenyl wherein the substituents are $C_1$ to $C_3$ alkyl, halogen, CN, $CF_3$, $COOR^{14}$, $CH_2COOR^{14}$, $C_1$ to $C_3$ alkoxy, or $C_1$ to $C_4$ perfluoroalkyl;
each $R^{14}$ is independently H, phenyl, benzyl or $C_1$ to $C_6$ alkyl; and,
each $R^{15}$ independently is H, $(CH_2)_mCOOR^{14}$ wherein m is 0 to 4, $C_1$ to $C_6$ alkyl, $CF_3$, phenyl, or substituted phenyl wherein substituted phenyl is as defined above in the definition of $R^{13}$;
or a pharmaceutically acceptable salt thereof.

Preferred compounds of the present invention comprise the compounds of formula I wherein:
$R^1$, $R^2$, $R^3$, $R^4$, $R^5$ and $R^6$ are each independently selected from:

(1) hydrogen;
(2) alkyl having 1 to 6 carbon atoms;
(3) alkenyl having 2 to 6 carbon atoms;
(4) —(CH$_2$)$_n$M wherein n is 0 or 1 and M is as defined previously for Formula I;

R$^{10}$ is COOH; CH$_2$OH; CHO; tetrazole; CONH-SO$_3$R$^{11}$ wherein R$^{11}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or acyl to 1 to 6 carbons; hydroxymethylketone; CN; or CON(R$^9$)$_r$;

r is 1 to 6; and the remaining substituents are as defined previously for Formula I.

More preferred compounds of the present invention comprise the compounds of Formula I. wherein:

R$^1$, R$^2$, R$^3$, R$^4$, R$^5$ and R$^6$ are each independently selected from:
(1) hydrogen;
(2) alkyl having 1 to 6 carbon atoms;
(3) alkenyl having 2 to 6 carbon atoms;
(4) M wherein M is as defined initially for Formula I;

R$^{10}$ is COOH; CH$_2$OH; CHO; tetrazole; hydroxymethylketone;

r is 1 or 2; and the remaining substituents are as defined initially for Formula I.

Most preferred compounds of the present invention comprise the compounds of Formula I. wherein:

R$^1$, R$^2$, R$^3$, R$^4$, R$^5$ and R$^6$ are each independently selected from:
(1) hydrogen;
(2) alkyl having 1 to 6 carbon atoms;
(3) M wherein M is
a) OR$^{13}$;
b) halogen;
c) CF$_3$;
d) SR$^{13}$;
e) COOR$^{14}$;
f)

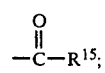

g) tetrazole;
h) —SOR$^{13}$;
i) —CONR$^{14}$R$^{14}$;
j) —SO$_2$NR$^{14}$R$^{14}$;
k) —SO$_2$R$^{13}$;
l)

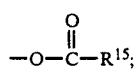

m) CN;
n) N$_3$;

each R$^9$ is independently H, or alkyl of 1 to 4 carbons;
R$^{10}$ is COOH; or tetrazole;
r is 1 and the remaining substituents are as defined initially for Formula I.

In the above most preferred embodiment, those compounds are particularly preferred wherein at least one of R$^1$ to R$^4$ is not hydrogen; one of R$^5$ or R$^6$ is not hydrogen; R$^7$ is hydrogen; R$^9$ is hydrogen, and the remaining substituents are as defined in the most preferred embodiment.

What is claimed is:
1. A compound of the formula:

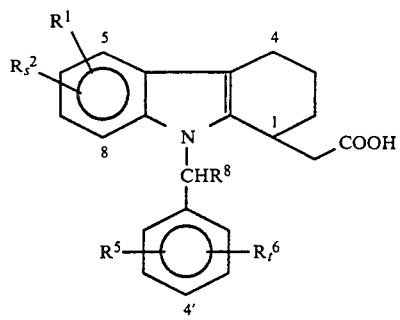

wherein:
R$^1$ is H, C$_1$–C$_6$ alkyl, OR$^{13}$, F, Cl, or Br;
R$^2$ is H, Cl, F, or Br;
R$^5$ is H, Cl, or OR$^{13}$;
R$^6$ is H or Cl;
R$^8$ is H or C$_1$–C$_6$ alkyl;
R$^{13}$ is C$_1$–C$_6$ alkyl;
s is 0 when R$^1$ is C$_1$–C$_6$ alkyl or OR$^{13}$;
s is 1 when R$^1$ is H, F, Cl, or Br;
t is 0 when R$^5$ is OR$^{13}$;
t is 1 when R$^5$ is H or Cl;
or a pharmaceutically acceptable salt thereof.

2. Compound of claim 1 which is:
9-p-chlorobenzyl-6-fluoro-1,2,3,4-tetrahydrocarbazol-1-yl-acetic acid;
9-p-chlorobenzyl-6-methoxy-1,2,3,4-tetrahydrocarbazol-1-yl-acetic acid;
(−)9-p-chlorobenzyl-6-fluoro-1,2,3,4-tetrahydrocarbazol-1-yl-acetic acid
(+)9-p-chlorobenzyl-6-fluoro-1,2,3,4-tetrahydrocarbazol-1-yl-acetic acid;
9-benzyl-6-fluoro-1,2,3,4-tetrahydrocarbazol-1-yl-acetic acid;
9-p-methoxybenzyl-6-fluoro-1,2,3,4-tetrahydrocarbazol-1-yl-acetic acid;
9-(3,4-dichloro)benzyl-6-fluoro-1,2,3,4-tetrahydrocarbazol-1-yl-acetic acid;
9-[1-(1-phenyl)ethyl]-6-fluoro-1,2,3,4-tetrahydrocarbazol-1-yl-acetic acid;
9-p-chlorobenzyl-1,2,3,4-tetrahydrocarbazol-1-yl-acetic acid;
9-p-chlorobenzyl-6-chloro-1,2,3,4-tetrahydrocarbazol-1-yl-acetic acid;
9-p-chlorobenzyl-8-methyl-1,2,3,4-tetrahydrocarbazol-1-yl-acetic acid;
6-bromo-9-p-chlorobenzyl-1,2,3,4-tetrahydrocarbazol-1-yl-acetic acid;
9-p-chlorobenzyl-6-methyl-1,2,3,4-tetrahydrocarbazol-1-yl acetic acid;
9-p-chlorobenzyl-8-fluoro-1,2,3,4-tetrahydrocarbozol-1-yl-acetic acid;
9-p-chlorobenzyl-5-fluoro-1,2,3,4-tetrahydrocarbazol-1-yl-acetic acid;
9-p-chlorobenzyl-7-fluoro-1,2,3,4-tetrahydrocarbazol-1-yl-acetic acid;
9-p-chlorobenzyl-5,7-dichloro-1,2,3,4-tetrahydrocarbazol-1-yl-acetic acid;
9-p-chlorobenzyl-6,8-dichloro-1,2,3,4-tetrahydrocarbazol-1-yl-acetic acid;
9-p-chlorobenzyl-6-isopropyl-1,2,3,4-tetrahydrocarbazol-1-yl-acetic acid;

9-p-chlorobenzyl-6-tert-butyl-1,2,3,4-tetrahydrocarbazol-1-yl-acetic acid;
9-p-chlorobenzyl-8-isopropyl-1,2,3,4-tetrahydrocarbazol-1-yl-acetic acid;
9-p-chlorobenzyl-6,8-difluoro-1,2,3,4-tetrahydrocarbazol-1-yl-acetic acid;
(−)-9-p-chlorobenzyl-6,8-difluoro-1,2,3,4-tetrahydrocarbazol-1-yl-acetic acid;
(+)-9-p-chlorobenzyl-6,8-difluoro-1,2,3,4-tetrahydrocarbazol-1-yl-acetic acid;
(−)-9-p-chlorobenzyl-8-methyl-1,2,3,4-tetrahydrocarbazol-1-yl-acetic acid;
(+)-9-p-chlorobenzyl-8-methyl-1,2,3,4-tetrahydrocarbazol-1-yl-acetic acid;
(−)-9-p-chlorobenzyl-8-fluoro-1,2,3,4-tetrahydrocarbazol-1-yl-acetic acid;
(+)-9-pchlorobenzyl-8-fluoro-1,2,3,4-tetrahydrocarbazol-1-yl-acetic acid;
9-o-chlorobenzyl-6,8-difluoro-1,2,3,4-atetrahydrocarbazol-1-yl-acetic acid;
9-(2,4-dichlorobenzyl)-6,8-difluoro-1,2,3,4-tetrahydrocarbazol-1-yl-acetic acid;
9-m-chlorobenzyl-6,8-difluoro-1,2,3,4-tetrahydrocarbazol-1-yl-acetic acid.

3. A compound of claim 1 which is:
9-p-chlorobenzyl-6-fluoro-1,2,3,4-tetrahydrocarbazol-1-yl-acetic acid;
9-p-chlorobenzyl-8-methyl-1,2,3,4-tetrahydrocarbazol-1-yl-acetic acid;
9-p-chlorobenzyl-8-fluoro-1,2,3,4-tetrahydrocarbazol-1-yl-acetic acid; or
9-p-chlorobenzyl-6,8-difluoro-1,2,3,4-tetrahydrocarbazol-1-yl-acetic acid.

4. A compound of claim 1, which is a pure optical isomer.
5. A compound of claim 4, which is the (+)-isomer.
6. A compound of claim 4, which is the (−)-isomer.
7. A compound of claim 6 which is:
(−)9-p-chlorobenzyl-6-fluoro-1,2,3,4-tetrahydrocarbazol-1-yl-acetic acid;
(−)-9-chlorobenzyl-6,8-difluoro-1,2,3,4-tetrahydrocarbazol-1-yl-acetic acid;
(−)-9-p-chlorobenzyl-8-methyl-1,2,3,4-tetrahydrocarbazol-1-yl-acetic acid; or
(−)-9-p-chlorobenzyl-8-fluoro-1,2,3,4-tetrahydrocarbazol-1-yl-acetic acid.

8. A compound of the formula:

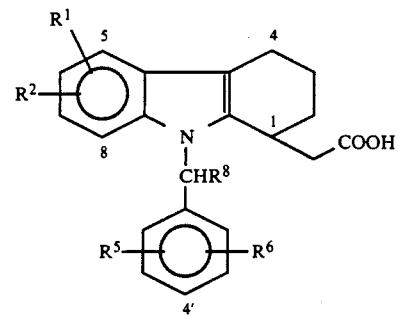

wherein:

| Compound | R¹ | R² | R⁵ | R⁶ | R⁸ |
|---|---|---|---|---|---|
| 1 (Ex. 1) | 6-F | H | 4'-Cl | H | H |
| 2 (Ex. 4) | 6-OMe | H | 4'-Cl | H | H |
| 3 (Ex. 7) | 6-F (−)isomer | H | 4'-Cl | H | H |
| 4 (Ex. 8) | 6-F (+)isomer | H | 4'-Cl | H | H |
| 5 (Ex. 9) | 6-F | H | H | H | H |
| 6 (Ex. 10) | 6-F | H | 4'-OMe | H | H |
| 7 (Ex. 11) | 6-F | H | 3'-Cl | 4'-Cl | H |
| 8 (Ex. 12) | 6-F | H | H | H | Me |
| 9 (Ex. 13) | H | H | 4'-Cl | H | H |
| 10 (Ex. 14) | 6-Cl | H | 4'-Cl | H | H |
| 11 (Ex. 15) | 8-Me | H | 4'-Cl | H | H |
| 12 (Ex. 16) | 6-Br | H | 4'-Cl | H | H |
| 13 (Ex. 17) | 6-Me | H | 4'-Cl | H | H |
| 14 (Ex. 19) | 8-F | H | 4'-Cl | H | H |
| 16 (Ex. 21) | 5-F | H | 4'-Cl | H | H |
| 17 (Ex. 21) | 7-F | H | 4'-Cl | H | H |
| 18 (Ex. 22) | 5-Cl | 7-Cl | 4'-Cl | H | H |
| 19 (Ex. 23) | 6-Cl | 8-Cl | 4'-Cl | H | H |
| 23 | 8-Br | H | 4'-Cl | H | H |
| 24 (Ex. 24) | 6-CH(Me)₂ | H | 4'-Cl | H | H |
| 25 (Ex. 25) | 6-C(Me)₃ | H | 4'-Cl | H | H |
| 30 (Ex. 30) | 8-CH(Me)₂ | H | 4'-Cl | H | H |
| 34 (Ex. 34) | 6-F | 8-F | 4'-Cl | H | H |
| 37 (Ex. 37) | 6-F (−)isomer | 8-F | 4'-Cl | H | H |
| 38 (Ex. 38) | 6-F (+)isomer | 8-F | 4'-Cl | H | H |
| 39 (Ex. 39) | 8-Me (−)isomer | H | 4'-Cl | H | H |
| 40 (Ex. 40) | 8-Me (+)isomer | H | 4'-Cl | H | H |
| 41 (Ex. 41) | 8-F (−)isomer | H | 4'-Cl | H | H |
| 42 (Ex. 42) | 8-F (+)isomer | H | 4'-Cl | H | H |
| 43 | 6-F | 8-F | 3'-Cl | 4'-Cl | H |
| 44 | 6-F | 8-F | 2'-Cl | 4'-Cl | H |
| 45 | 6-F | 8-F | 4'-OMe | H | H |
| 65 (Ex. 45) | 6-F | 8-F | 2'-Cl | H | H |
| 68 (Ex. 54) | 6-F | 8-F | 3'-Cl | H | H |

9. A pharmaceutical composition which comprises a compound of claim 1 and a pharmaceutically acceptable carrier.

* * * * *